ized Patent (12) United States Patent Gordon et al.

(10) Patent No.: US 8,348,930 B2
(45) Date of Patent: Jan. 8, 2013

(54) FLUID DELIVERY DEVICE WITH A DIFFUSION MEMBRANE AND ELECTROCHEMICAL PUMP

(75) Inventors: John Howard Gordon, Salt Lake City, UT (US); Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 281 days.

(21) Appl. No.: 12/721,636

(22) Filed: Mar. 11, 2010

(65) Prior Publication Data

US 2010/0222770 A1 Sep. 2, 2010

Related U.S. Application Data

(63) Continuation-in-part of application No. 11/160,650, filed on Jul. 1, 2005, now Pat. No. 7,896,687, which is a continuation-in-part of application No. 10/908,804, filed on May 26, 2005, now Pat. No. 7,458,965, which is a continuation-in-part of application No. 10/137,661, filed on May 1, 2002, now Pat. No. 7,470,267.

(51) Int. Cl.
*A61K 9/22* (2006.01)
(52) U.S. Cl. .................................................. 604/892.1
(58) Field of Classification Search .... 604/890.1–892.1, 604/500–502
See application file for complete search history.

(56) References Cited

U.S. PATENT DOCUMENTS

| | | | |
|---|---|---|---|
| 2,636,852 A | 4/1953 | Juda et al. | |
| 3,845,770 A | 11/1974 | Theeuwes et al. | |
| 3,894,538 A | 7/1975 | Richter | |
| 3,923,426 A | 12/1975 | Theeuwes | |
| 3,995,632 A | 12/1976 | Nakano et al. | |
| 4,140,122 A | 2/1979 | Kuhl et al. | |
| 4,505,710 A | 3/1985 | Collins | |
| 4,522,698 A | 6/1985 | Maget | |
| 4,549,947 A | 10/1985 | Inoue et al. | |
| 4,552,561 A | 11/1985 | Eckenhoff et al. | |
| 4,593,534 A | 6/1986 | Bloomfield | |
| 4,657,536 A * | 4/1987 | Dorman | 604/247 |
| 4,687,423 A | 8/1987 | Maget et al. | |
| 4,874,388 A * | 10/1989 | Wong et al. | 604/891.1 |
| 4,886,514 A * | 12/1989 | Maget | 604/891.1 |
| 4,902,278 A * | 2/1990 | Maget et al. | 604/132 |
| 5,030,216 A | 7/1991 | Theeuwes et al. | |
| 5,088,977 A | 2/1992 | Sibalis | |

(Continued)

OTHER PUBLICATIONS

Anderson, "Office Action for U.S. Appl. No. 11/173,813 sent Sep. 13, 2007", 1-12. Anderson, "Office Action for U.S. Appl. No. 11/173,813 sent Apr. 30, 2008", 1-10.

(Continued)

*Primary Examiner* — Kevin C Sirmons
*Assistant Examiner* — Bradley Osinski
(74) *Attorney, Agent, or Firm* — David Fonda

(57) ABSTRACT

A fluid delivery device can be used to deliver fluid within a living body. The fluid delivery device includes an electrochemical pump, a reservoir, a displaceable member, and a diffuse membrane. The electrochemical pump transports water and includes an electrochemical pump product chamber to retain water transported by the electrochemical pump. The reservoir contains a fluid to be delivered. The displaceable member is positioned between the electrochemical pump product chamber and the reservoir. The displaceable member is responsive to the electrochemical pump transporting water into the electrochemical pump product chamber. The diffuse membrane generates increased pressure within the electrochemical pump product chamber.

47 Claims, 13 Drawing Sheets

U.S. PATENT DOCUMENTS

| | | | |
|---|---|---|---|
| 5,167,613 | A | 12/1992 | Karami et al. |
| 5,242,565 | A | 9/1993 | Winsel |
| 5,279,608 | A | 1/1994 | Cheikh |
| 5,312,389 | A | 5/1994 | Theeuwes et al. |
| 5,707,361 | A | 1/1998 | Slettenmark |
| 5,707,499 | A | 1/1998 | Joshi et al. |
| 5,744,014 | A | 4/1998 | Gordon et al. |
| 5,746,064 | A | 5/1998 | Tsenter |
| 5,785,688 | A | 7/1998 | Joshi et al. |
| 5,788,826 | A | 8/1998 | Nyberg |
| 5,891,097 | A | 4/1999 | Saito et al. |
| 5,925,030 | A | 7/1999 | Gross et al. |
| 5,938,640 | A | 8/1999 | Maget et al. |
| 5,951,538 | A | 9/1999 | Joshi et al. |
| 6,060,196 | A | 5/2000 | Gordon et al. |
| 6,120,665 | A | 9/2000 | Chiang et al. |
| 6,163,720 | A | 12/2000 | Gyory et al. |
| 6,287,295 | B1 | 9/2001 | Chen et al. |
| 6,289,241 | B1 | 9/2001 | Phipps |
| 6,327,426 | B1 | 12/2001 | Joshi et al. |
| 6,450,991 | B1 | 9/2002 | Bunt et al. |
| 6,491,684 | B1 * | 12/2002 | Joshi et al. ............. 604/892.1 |
| 6,575,961 | B2 | 6/2003 | Joshi |
| 6,576,362 | B2 | 6/2003 | Hanlon |
| 6,740,077 | B1 * | 5/2004 | Brandau et al. ........... 604/892.1 |
| 6,872,292 | B2 | 3/2005 | Theeuwes et al. |
| 7,371,229 | B2 | 5/2008 | Theeuwes et al. |
| 2003/0205582 | A1 | 11/2003 | Joshi et al. |
| 2004/0241528 | A1 | 12/2004 | Chiao et al. |
| 2006/0052768 | A1 | 3/2006 | Joshi et al. |
| 2006/0116641 | A1 | 6/2006 | Gordon et al. |
| 2006/0116663 | A1 | 6/2006 | Joshi |
| 2008/0102119 | A1 | 5/2008 | Grovender et al. |
| 2009/0281528 | A1 | 11/2009 | Grovender et al. |

OTHER PUBLICATIONS

Anderson, Michael J., "Office Action for U.S. Appl. No. 11/173,813 Dated Jan. 9, 2007", 1-13.

Anderson, Michael J., "Office Action for U.S. Appl. No. 11/173,813 sent Jun. 23, 2009", 1-11.

Anderson, Michael J., "Office Action for U.S. Appl. No. 11/173,813 sent Dec. 10, 2008", 1-8.

Bouchelle, "Office Action for U.S. Appl. No. 10/137,661 sent Apr. 24, 2006", 1-7.

Bouchelle, Laura A., "Office Action for U.S. Appl. No. 10/137,661 Dated Dec. 20, 2006", 1-9.

Bouchelle, Laura A., "Office Action for U.S. Appl. No. 10/908,804 Dated Jan. 3, 2007", 1-9.

Copenheaver, "International Search Report for PCT/US06/20570 sent Nov. 22, 2006", 1-2.

Copenheaver, "Written Opinion for PCT/US06/20570 sent Nov. 22, 2006", 1-4.

Greene, "International Search Report for PCT/US06/22502 sent May 21, 2007", 1-2.

Greene, "Written Opinion for PCT/US06/22502 sent May 21, 2007", 1-3.

Koharski, Christopher "Office Action for U.S. Appl. No. 10/353,769 sent Sep. 11, 2006", 1-9.

Koharski, Christopher "Office Action for U.S. Appl. No. 10/353,769 sent Apr. 17, 2007", 1-11.

Lucchosi, Nicholas "Written Opinion of the International Searching Authority", PCT/US06/25502, (May 21, 2007),1-3.

Young, "International Search Report for PCT/US 6/26006 sent Jun. 3, 2008", 1-2.

Young, "Written Opinion for PCT/US 6/26006 sent Jun. 3, 2008", 1-4.

* cited by examiner

FLUID DELIVERY DEVICE WITH A DIFFUSION MEMBRANE AND ELECTROCHEMICAL PUMP

CROSS-REFERENCE TO RELATED APPLICATIONS

This application is a continuation-in-part of U.S. application Ser. No. 11/160,650, now U.S. Pat. No. 7,896,687, filed on Jul. 1, 2005, and entitled "Fluid Delivery Device Having an Electrochemical Pump with an Ion-Exchange Membrane and Associated Method," which is a continuation-in-part of U.S. application Ser. No. 10/908,804, now U.S. Pat. No. 7,458,965, filed on May 26, 2005, which is a continuation-in-part of U.S. application Ser. No. 10/137,661, now U.S. Pat. No. 7,470,267, filed on May 1, 2002; the contents of these applications are expressly incorporated by reference herein in their entirety.

BACKGROUND

Embodiments described herein relate in general to a fluid delivery device that includes an electrochemical pump for controllably delivering small volumes of fluid with high precision and accuracy. The fluid delivery rate of the device can also be changed during operation.

In many medical situations, it may be necessary or at least desirable to deliver small amounts of fluids and/or chemical agents over a relatively long period of time. Such fluids may include biologicals, drugs, lubricants, fragrant fluids, and chemical agents. A common example of such an application is the gradual administration of a pharmaceutical agent into the living (e.g., human) body. A very common and traditional apparatus for the gradual administration of fluid into the human body is an intravenous administration set in which gravity induced hydrostatic infusion dispenses a fluid from a familiarly suspended bottle or bag above the patient.

Other methods for the gradual administration of fluids have been devised to eliminate the need for suspending the fluid above the patient and thereby provide the patient with greater mobility. One such method utilizes a diffusion controlled delivery pump wherein the fluid diffuses through a membrane at a constant rate. The rate of delivery may be adjusted by varying the nature of the membrane and the concentration of the solution in contact with the membrane, e.g., a transdermal drug delivery patch. Additional transdermal technologies include: iontophoresis, in which low voltage electrical current is utilized to drive charged drugs through the skin; electroporation, in which short electrical pulses of high voltage is utilized to create transient aqueous pores in the skin; sonophoresis, in which low frequency ultrasonic energy is utilized to disrupt the stratum corneum; and thermal energy, in which heat is utilized to make the skin more permeable and to increase the energy of drug molecules. Even magnetic energy, or magnetophoresis, has been investigated as a way to increase drug flux across the skin. Of these transdermal technologies, only iontophoresis has been successfully developed into a marketable product, albeit for local pain relief. A transdermal system may not be the preferred method for gradually administering fluids in every case, and various factors should be considered that may affect its usefulness, such as: the adhesive utilized to secure the system to the individual may not adhere well to all types of skin; some drug formulations may cause skin irritation or allergy; the transdermal system may be uncomfortable to wear or too costly; and some drugs that require high blood levels (low potency) cannot be properly administered.

A mechanical pump dispenser is yet another mechanism for gradually administering fluids to an individual. The conventional mechanical pump dispenser utilizes various types of mechanical pumps to expel the fluid from a reservoir. Some processes incorporating a mechanical pump dispenser include: a continuous intravenous infusion pump system, for example from Intevac Inc.; an epidural infusion system; and a subcutaneous infusion system, e.g., utilizing a portable insulin infusion pump. An externally worn pump is also conventionally used with a transcutaneous catheter; however, the external pump is often bulky and inconvenient because it is typically strapped onto the wearer, or carried on a belt or in a harness. A common drawback of the mechanical pump is that the required entry site into the body is susceptible to infection. In addition, most mechanical pumps are designed to deliver relatively large quantities of fluid and do not effectively dispense small volumes over longer time periods.

Other fluid delivery processes utilize pressure to administer a fluid to the individual. For instance, a charged reservoir dispenser stores a fluid under pressure in a flexible reservoir and then selectively expels the fluid by the force of internal reservoir pressure—the rate of release is often regulated by a plurality of complex valve systems. The pressurized gas dispenser implements a pressurized gas to expel the fluid, while an osmotic dispenser relies on a solute that exhibits an osmotic pressure gradient against water to dispense the fluid. The OROS® system produced by ALZA Corporation is an example of an osmotically driven system in which osmosis is the energy source for drug delivery. In the OROS® system, the drug solution flows from a tablet at a constant zero-order rate as the tablet progresses through the gastro-intestinal (GI) tract until the entire solid drug in the core is dissolved or until the unit is eliminated. In vivo and in vitro testing has shown that the delivery rate is independent of GI motility, pH, and food in the gastro-intestinal tract. The release of the drug is controlled by the solubility of the drug in gastric fluid, the osmotic pressure of the core formulation, and the dimensions and permeability of the membrane.

In addition to the above-identified fluid administration device types or techniques, there are a number of conventional implantable drug delivery pumps and systems. One widely used implant is the large capacity (18 mL) programmable electromechanical SynchroMed® pump. While applicable in a number of therapies, several drawbacks of the SynchroMed® pump are its cost, the overall cost of the therapy, and that surgery is required for placement of the large pump.

Smaller sized implantable drug delivery pumps are also available such as the osmotic pump of the DUROS® system. Generally, the osmotic pump involves imbibing water or another driving fluid. The pump includes three chambers: a salt chamber, a water chamber, and a fluid chamber. The salt and water chambers are separated by a semi-permeable membrane. This configuration creates a high osmotic driving force, e.g., environmental osmosis, for water transport across the membrane. This membrane is permeable to water, but impermeable to salt. The fluid chamber is separated from the other two chambers by a flexible diaphragm. Water imbibes osmotically into the salt chamber creating substantial hydrostatic pressures, which in turn exert a force on the displaceable member, e.g., diaphragm—thus expelling the fluid. The use of osmotic pumps is typically directed to applications for constant fluid delivery. In order to vary the fluid flow, it is often necessary to provide numerous osmotic pumps with differing outputs. The osmotic pump also requires charging—the time required for liquid to diffuse through the semipermeable membrane and begin dissolving the osmagent at steady state—which in turn delays delivery of the active and further limits its suitability for instantaneous or emergency use. The fluid delivery rate of the osmotically driven device typically cannot be changed or turned off. In other words, it possible to shut off the delivery of the fluid after commencement of delivery.

With further reference to some specific types of conventional osmotic pumps, water is imbibed osmotically through a membrane into a salt chamber pressurizing a piston to expand into a drug chamber to force a drug out through a delivery orifice. The driving force behind the drug delivery of this pump is osmotic pressure, which can be as high as 200 atmospheres depending on the salt used, even though the pressure required to disperse the drug from the device is small and the drug delivery rate remains constant as long as some excess undissolved salt remains in the salt chamber. In comparison with mechanically driven devices, osmotic systems are small, simple, reliable, and less expensive to manufacture. Because of the small size of the osmotic system, it can be implanted during a simple procedure in the physician's office. On the other hand, the fixed delivery rate of the conventional osmotic pump in not adjustable during its operation.

In addition to osmotic pumps, some forms of electro-osmotic pumps are used. An electro-osmotic pump is an electrolytic cell having a permselective ion exchange membrane and therefore requires an external DC power source to drive the electrode reactions. In some conventional embodiments, an electrochemically driven fluid dispenser based on electroosmotic fluid transport. The pump includes a plastic housing having a fluid inlet and outlet, a pair of spaced silver-silver chloride electrodes disposed in the housing and connected to a DC power source, a porous ceramic plug that has a high zeta potential relative to the fluid, a cation exchange membrane positioned on each side of the ceramic plug between it and the electrode facing it, and a passageway in the housing extending from the fluid inlet to one side of the plug and from the other side of the plug to the outlet. When a potential difference is applied across the anode and cathode, the transport fluid will flow through the porous plug from the anode to the cathode. One particular disadvantage of this electro-osmotic pump with a porous plug is that the delivery pressures are very low, well below 0.5 ATM. In addition, any ions in the driving fluid will substantially affect the zeta potential and reduce the electro-osmotic flow. Another disadvantage of this electro-osmotic pump is that it requires an external DC power source that lessens the overall volume efficiency of the fluid delivery device.

Gas generating devices that are both portable and accurate for dispensing small volumes are also used in drug delivery systems. These gas-generating methods include galvanic cells and electrolytic cells. By definition, a galvanic cell is an electrochemical cell that requires no externally applied voltage to drive the electrochemical reactions. In galvanic gas generating cells, hydrogen or oxygen gas is formed at the cathode or anode, respectively, as a result of a reaction between a metal or metal oxide and an aqueous electrolyte. Typically, the anode and cathode of the galvanic cell are connected through a resistor that regulates the current passed through the cell, and in turn, directly regulates the production of gas that exerts a force on a diaphragm or piston—thereby expelling the drug.

Other conventional delivery systems are based on the use of galvanic hydrogen generating cell. In these types of cells, a zinc anode reacts with an alkaline electrolyte producing zinc oxide and water molecules are reduced on a porous carbon electrode producing gaseous hydrogen. In other conventional cells, a galvanic oxygen-generating cell that is constructed much like a zinc/air button cell, in which a reducible oxide is reduced at the cathode while hydroxyl ions are formed. The hydroxyl ions oxidize at the anode and release oxygen.

In contrast to the galvanic cell, an electrolytic cell uses an external DC power source to drive the electrochemical reactions. When voltage is applied to the electrodes, the electrolyte gives off a gas that exerts a force on a diaphragm or piston, thus expelling the fluid. At least three types of electrolytic gas generating cells have been proposed for use in fluid delivery devices. A first type is based on water electrolysis requiring an operating voltage over 1.23 V. A second type, also known as oxygen and hydrogen gas pumps, uses a lower DC voltage than that utilized in water electrolysis systems. Both of these cell types utilize an ion exchange polymer membrane. A third type of gas generating electrolytic cell is based on the use of an electrolytically decomposable chemical compound that produces a reduced metal at the cathode, and generates gaseous oxygen by oxidation of water at the anode.

Another type of device is an electrochemically driven fluid dispenser based on the electrolysis of water. In this dispenser, water is contained in an electrochemical cell in which porous metal electrodes are joined to both sides of a solid polymer cation exchange membrane, and both of the two electrodes are made to contact with the water so as to use oxygen or hydrogen generated from an anode or cathode respectively, upon current conduction. Thus, hydrogen, oxygen, or a gas mixture of hydrogen and oxygen—generated by electrolysis of water when a DC current is made to flow between the electrodes—is used as a pressurization source of the fluid dispenser.

Electrochemical oxygen and hydrogen pumps are constructed in a similar manner to the above-discussed water electrolysis cell. Conventional electrochemically driven fluid dispensers have an electrochemical cell in which porous gas diffusion electrodes are joined respectively to the opposite surfaces of an ion exchange membrane containing water functioning as an electrolyte. The electrochemically driven fluid dispenser uses such a phenomenon that when hydrogen is supplied to an anode of the electrochemical cell and a DC current is made to flow between the anode and the cathode, the hydrogen becomes hydrogen ions at the anode. When the produced hydrogen ions reach the cathode through the ion exchange membrane, an electrochemical reaction arises to generate gaseous hydrogen. Since the net effect of these processes is the transport of hydrogen from one side of the membrane to the other, this cell is also called a hydrogen pump. The hydrogen generated and pressurized at the cathode is used as a driving source for pushing a displaceable member, e.g., a piston, a diaphragm, or the like. Alternatively, oxygen may be used in place of hydrogen as a reactant in this type of electrochemical cell, so that the cell then acts as an oxygen pump. Thus, oxygen is reduced on one side of a water-containing electrolytic cell and water is oxidized on the opposite side to generate molecular oxygen, wherein the molecular oxygen so generated is used as the propellant to force liquid from an adjacent reservoir.

A gas generating electrolytic cell using an electrolytically decomposable chemical compound that produces a reduced metal at the cathode and generates gaseous oxygen by water oxidation at the anode is also known. This type of cell generally includes a graphite anode, an aqueous electrolyte, and a copper hydroxide cathode. As electrical current passes through a circuit in which the cell is connected, copper is plated out in the cathode and oxygen is released at the anode. To ensure storage stability, an active cathode material is selected such that the cells use an applied voltage for the electrochemical reactions to proceed. A battery cell is provided in the circuit to drive the current through the gas-generating cell. The rate of oxygen generated at the anode is directly proportional to the current and acts as a pressurizing agent to perform the work of expelling a fluid from a bladder or other fluid-containing reservoir, which has a movable wall that is acted upon as the gas is generated.

While the above-identified electrochemically driven fluid delivery devices are operable for certain applications, they are not optimal for others. In particular, gas generating cell based pumps are sensitive to temperature and atmospheric pressure. For this reason, osmotic and electro-osmotic pumps are often more appropriate.

SUMMARY

Based on the shortcomings of conventional devices, there is a need for an implantable volume efficient fluid dispenser including a highly accurate programmable delivery mechanism that can be quickly adjusted to change its delivery rate as desired. In some embodiments described herein, the delivery mechanism occupies a small portion of the fluid dispenser, is capable of delivering small volumes of fluid with precision and accuracy, and/or is impervious to barometric pressure and temperature.

Embodiments of a system are described. In one embodiment, the system is a fluid delivery device which can be used to deliver fluid within a living body. The fluid delivery device includes an electrochemical pump, a reservoir, a displaceable member, and a diffuse membrane. The electrochemical pump transports water and includes an electrochemical pump product chamber to retain water transported by the electrochemical pump. The reservoir contains a fluid to be delivered. The displaceable member is positioned between the electrochemical pump product chamber and the reservoir. The displaceable member is responsive to the electrochemical pump transporting water into the electrochemical pump product chamber. The diffuse membrane generates increased pressure within the electrochemical pump product chamber.

In another embodiment, the fluid delivery device includes an electrochemical pump, a control circuit, an active electrode and an auxiliary electrode, a reservoir, a displaceable member, an ion-exchange membrane, a diffuse membrane, a protective porous separator, and a housing. The electrochemical pump transports water. The electrochemical pump includes an electrochemical pump product chamber to retain water transported by the electrochemical pump. The control circuit is operably connected to the electrochemical pump. A rate of water transport of the electrochemical pump is responsive to electrical current flowing through the control circuit. The active electrode and the auxiliary electrode are in ionic communication with each other and operably connected to the control circuit. The reservoir contains a fluid to be delivered. The displaceable member is positioned between the electrochemical pump product chamber and the reservoir. The displaceable member is responsive to the electrochemical pump transporting water into the electrochemical pump product chamber. The ion-exchange membrane is positioned between the active electrode and the auxiliary electrode. The ion-exchange membrane transports water by osmosis and electro-osmosis between the active electrode and the auxiliary electrode into the electrochemical pump product chamber. The diffuse membrane generates increased pressure within the electrochemical pump product chamber. The protective porous separator is permeable to $H_2O$ molecules or saline and positioned such that the active electrode or the ion-exchange membrane is indirectly exposed to body tissue or body fluids. The housing contains the electrochemical pump, the displaceable member, the diffuse membrane, and the reservoir therein. The auxiliary electrode is external to the housing. Other embodiments of the system are also described.

Embodiments of a method are also described. In one embodiment, the method is a method for delivering a fluid by a fluid delivery device suitable for implantation in a living body. An embodiment of the method includes transporting water through an ion-exchange membrane by osmosis and electro-osmosis using an electrochemical pump at a rate proportional to an output signal of a control circuit. The method also includes expanding a volume of an electrochemical pump product chamber in response to transporting the water into the electrochemical pump product chamber. The method also includes generating increased pressure within the expanded electrochemical pump product chamber using a diffuse membrane. The method also includes displacing a displaceable member in response to the pressure in the electrochemical pump product chamber. The method also includes controllably expelling fluid from the reservoir in response to displacement of the displaceable member. Other embodiments of the method are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
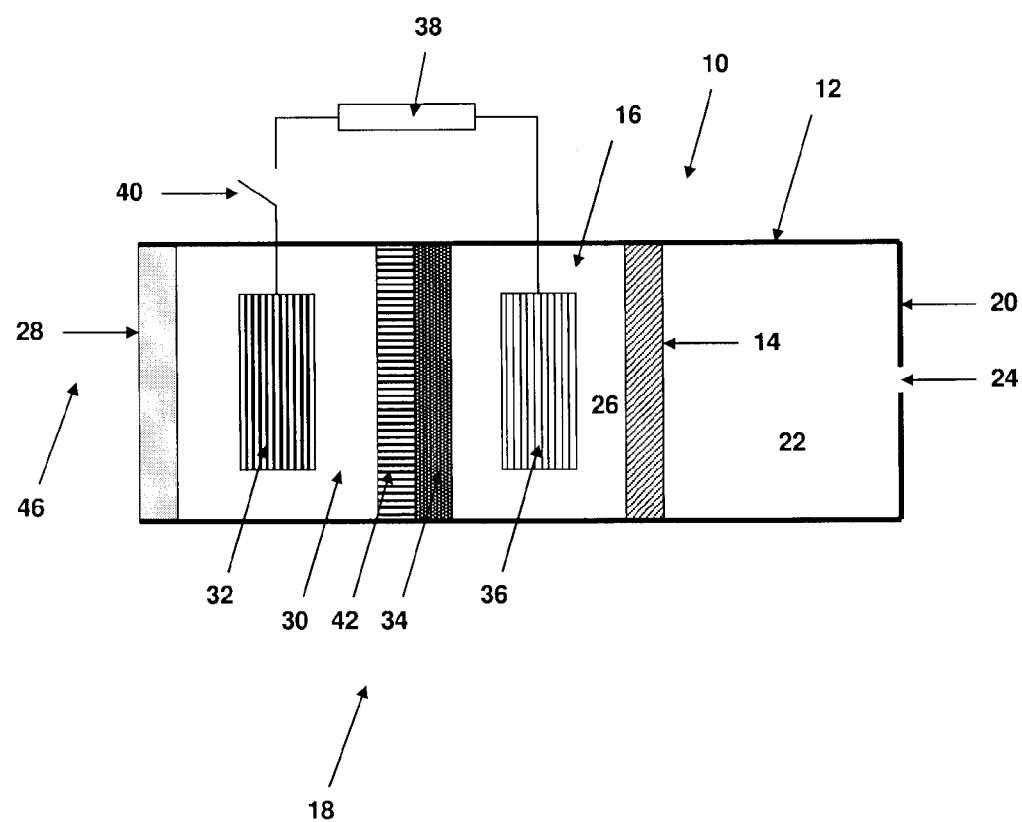
FIG. 1 depicts a cross-sectional schematic representation of one embodiment of a fluid delivery device having an ion exchange membrane.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Embodiments of the fluid delivery device described herein may be useful in implantable medical devices. These devices may be implanted within patients for delivery of medicament to the patient over a long period of time. Embodiments described herein can potentially be used for continuous, bolus intermittent pulse or periodic pulse (matching circadian, menstrual, ovulation or daily cycles) release of a drug or cell culture in a systemic or localized fashion. Some embodiments are capable of adjusting the fluid delivery rate based on the response of a sensor (e.g., a bio-feedback loop). Some embodiments can be used for delivering a fluid in various applications, including, but not limited to: parasite control, oncology drugs, pain management drugs, growth hormones, lobotomy (where a portion of the brain is selectively deteriorated by a delivered agent), antibiotics, DNA delivery, lactate hormone, cardioactive drugs, anti-malarial drugs, compliance medications such as antiabuse, vaccines, sexual dysfunction drugs, steroids, hormones, stimulants, or sleep aids. Some embodiments can also be used when provision is made for a device to contain water/electrolyte where the device is external to the body and delivery of a drug is via oral, anal, ear, nasal, or by piercing a part of the skin. Some embodiments can also be utilized in the form of a patch. Although embodiments described herein are generally described in conjunction with implantable devices, it should be noted that the teachings contained within this specification and the appended claims may be translated to other devices and applications without straying from the intended scope of this disclosure.

Referring now to the drawings and to FIG. 1 in particular, a first embodiment is shown wherein a fluid delivery device 10 comprises a reservoir 12, a displaceable member 14, an electrochemical pump product chamber 16, an electrochemical pump 18, and a housing 20. It is to be further understood that FIG. 1 (as well as FIGS. 9-12) is merely a schematic representation of the fluid delivery device 10 of the present invention and as such, some of the components have been distorted from their actual scale for pictorial clarity.

The reservoir 12 is capable of containing a fluid 22, such as a biological, drug, lubricant, fragrant fluid, chemical agent, or mixtures thereof, which is delivered upon displacement of the displaceable member 14. It will be understood that the term "fluid" is herein defined as a liquid, gel, paste, suspension (with or without dispersant), or other semi-solid state material that is capable of being delivered out of a reservoir. Solid forms such as rods or encapsulated pills, paint balls, depots can also be delivered. The fluid can be either layered or homogenous. In the layered form, different fluids can be made into layers and can be delivered in succession. The reservoir 12 may include one or more apertures 24—e.g., outlet and filling/refilling port—for directing delivery of the fluid 22 from the fluid delivery device 10. The reservoir 12 may be fabricated from any one of a number of materials, including, for example, metal, glass, natural and synthetic plastic, and composites.

A catheter or a plurality of catheters may be operably connected to the reservoir 12 and aperture(s) 24. The catheter may be long, short, flexible, perforated, contain an auxiliary electrode, contain a diffusion outlet or check valve to regulate pressure and flow rate, or be designed to serve as a reservoir.

The displaceable member 14 is positioned between the reservoir 12 and the electrochemical pump product chamber 16. The displaceable member 14 is shown in FIG. 1 as including a piston; however, other displaceable members that would be known to those having ordinary skill in the art having the present disclosure before them are likewise contemplated for use, including, but not limited to: a bladder, a diaphragm, a flexible bag, a bellows, a plunger, or combinations thereof. Alternatively, the fluid to be displaced may be contained within tubing in which a plunger (e.g., a ball) pushes fluid out of the tubing. The plunger may be a bubble, solid, separating fluid, bung, or gel.

The electrochemical pump product chamber 16 is positioned between the displaceable member 14 and the electrochemical pump 18, and is capable of containing water 26 that is controllably generated during operation of the electrochemical pump 18, as will be discussed in greater detail below. Similar to the reservoir 12, the electrochemical pump product chamber 16 may be fabricated from any one of a number of materials, such as metal, glass, natural and synthetic plastic, composites, etc.

The electrochemical pump 18 shown in FIG. 1 includes a protective porous separator 28, an auxiliary electrode compartment 30, an auxiliary electrode 32, an ion exchange membrane 34, an active electrode 36, an electric controller 38, an activation switch 40, and a support member(s) 42.

The protective porous separator 28 is positioned at an end of the fluid delivery device 10 distal from the reservoir 12. The purpose of this protective separator is to prevent unwanted species in the external fluid source 46 (e.g., body fluid) to come in direct contact with the electrode 32 and the ion-exchange membrane 34. The protective porous separator 28 is generally permeable to $H_2O$ molecules or saline from the body, and in cooperation with saline from the auxiliary electrode compartment 30, enables the water from the external source 46 (e.g., an inside of a living being's body) to diffuse or migrate into the auxiliary electrode compartment 30. The protective porous separator 28 may be fabricated from any one of a number of materials, including, but not limited to, metal, glass, natural and synthetic plastic, and composites. Additionally, a porous protective gel also generally permeable to $H_2O$ molecules or saline may be used to serve the purpose of the separator 28.

Alternatively, the auxiliary electrode 32 need not be positioned inside the device 10 and can be positioned either entirely away from the housing (FIG. 9) or on the outside wall of the device (FIG. 10), in which case the ion exchange membrane 34 has more direct access to the body fluid, and the porous separator 28 can be placed directly adjacent to the ion-exchange membrane 34 to prevent biofouling and to prevent unwanted species from directly contacting the ion-exchange membrane 34 directly. This alternative configuration may eliminate trapping of any unwanted solid, liquid, or gaseous species in the auxiliary compartment 30 and near the membrane.

While the use of the protective porous separator 28 is generally desirable for applications within the body, the separator 28 is not absolutely required, especially in the case where water or saline is self-contained in the auxiliary electrode compartment 30 without any migration of water from the external source 46. In this case, either a displaceable member 44 retracts (FIG. 11) or the flexible auxiliary electrode compartment 30 collapses around the auxiliary electrode 32 upon transfer of water from the auxiliary electrode chamber compartment 30 to the active electrode chamber 16 via electro-osmosis. In such an embodiment, the auxiliary electrode 32 can be exposed directly to fluid.

The ion-exchange membrane 34 can be in the form of a sheet, a hollow fiber, or a tube; and can be made from a polymer or a ceramic. Additionally, multiple membranes of the same type or types with differing functionalities and properties can be used. The electrical control circuit 38 (i.e., controller) is connected to the electrodes via conventional electrical conduit and directly controls the rate of water transfer from the external source 46 to the electrical pump product chamber 16.

The support member(s) 42 is a highly porous solid disk material that provides mechanical rigidity for the ion exchange membrane 34 and allows water to transport through it. The support member(s) 42 can be made of hard plastic, ceramic, glass, corrosion stable metal, e.g., titanium; or a combination thereof and can be in the form of a fabric, perforated plate, mesh, or a disk with a single or multiple holes. The support 42 can be a variety of shapes, including, but not limited to flat, concave, or convex.

The ion-exchange membrane 34 along with the support disk 42 is placed between the auxiliary electrode compartment 30 and the electrochemical pump product chamber 16 containing the active anode 36. The two compartments 16, 30 along with the ion-exchange membrane 34 there between can be sealed using gaskets, sealants, nipples, clamps, compression or by using ultrasonics, crimping, nipples, or clamp (not shown).

A controller 38 (i.e., control circuit) is operably connected to the electrodes 32, 36, varies the fluid delivery rate of the device 10, and can be positioned within the body, external to the body, or remote from the body. In simple form, the controller 38 can be a resistor, but may also be a more complex circuit, variable resistor, multi-position switch, wave form generator/processor, or switch that uses electromagnetic induction, RF signaling, infrared, magnetism, mechanics, or transduction for communication. As such, the controller 38 may or may not contain a battery. In one embodiment, an activation switch 40 is connected to the controller 38 and can be of the electronic, ionic, or mechanical type and capable of being controlled remotely via the controller 38.

Embodiments of the device 10 described herein may be configured in various shapes and forms and have additional features. Such shapes contemplated herein include, but are not limited to: tubular, coin, coil, planar, flexible bag form, hardball, jellyroll, and patch. And the additional features may include, but are not limited to: a pressure relief valve, a bio-feedback sensor, a remote battery, a locater, a problem indicator, a flow indicator, an anchor, an anti-biofouling sheath, a trocar, an extraction enhancer, an external switch, or an add-on to a stent. The device 10 can also be encased in a gel to avoid encapsulation and/or to promote diffusion of a drug.

Figure 9:
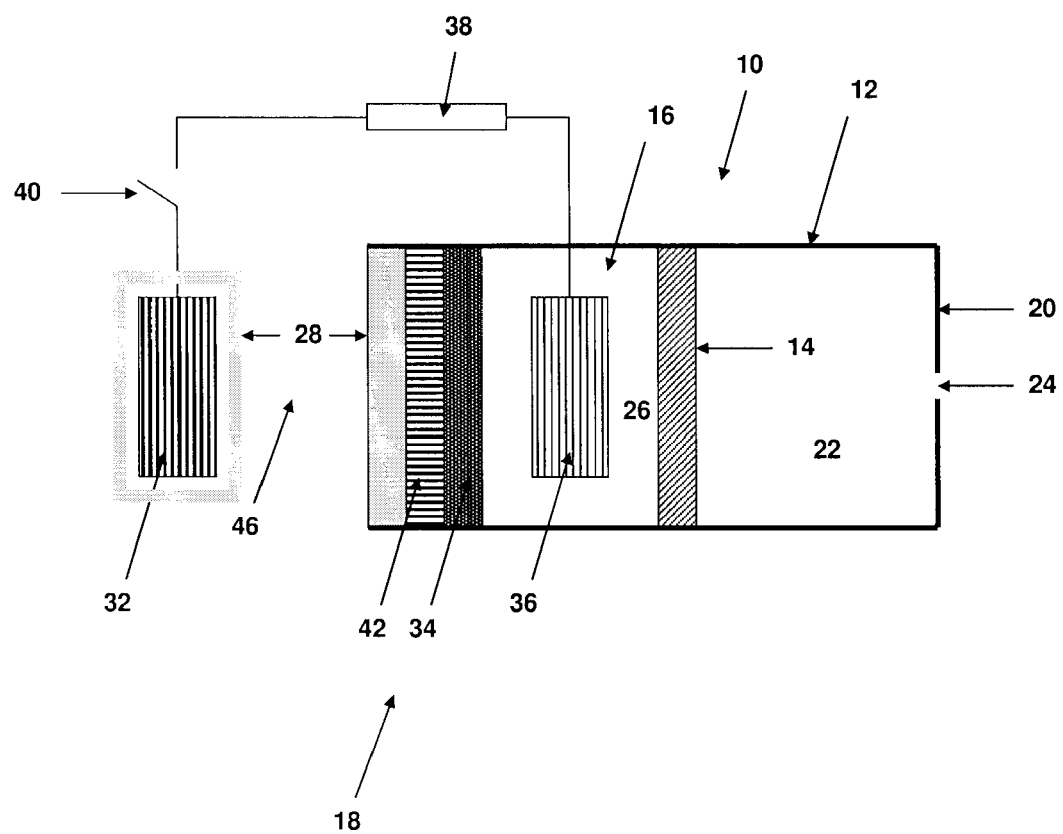
FIG. 9 depicts a cross-sectional side view of an alternative embodiment of a fluid delivery device having an external auxiliary electrode.
Figure 10:
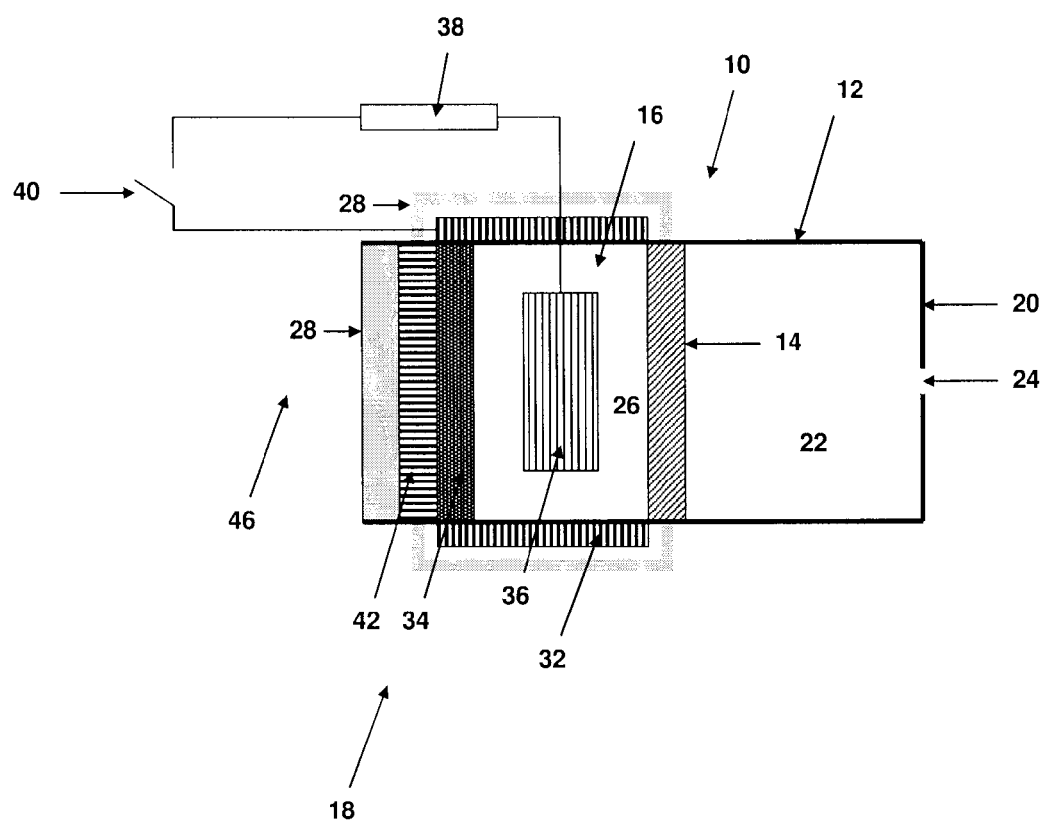
FIG. 10 depicts a cross-sectional side view of an alternative embodiment of a fluid delivery device having an external auxiliary electrode positioned on the external surface of the device.

In one embodiment, the auxiliary electrode 32, the ion-exchange membrane 34, and the active electrode 36 are respectively positioned adjacent to the protective porous separator 28. Alternatively, the auxiliary electrode 32 need not be positioned inside the device 10 and can be positioned either on the outside wall of the device or entirely away from the housing 20, as shown in FIGS. 9 and 10.

Figure 11:
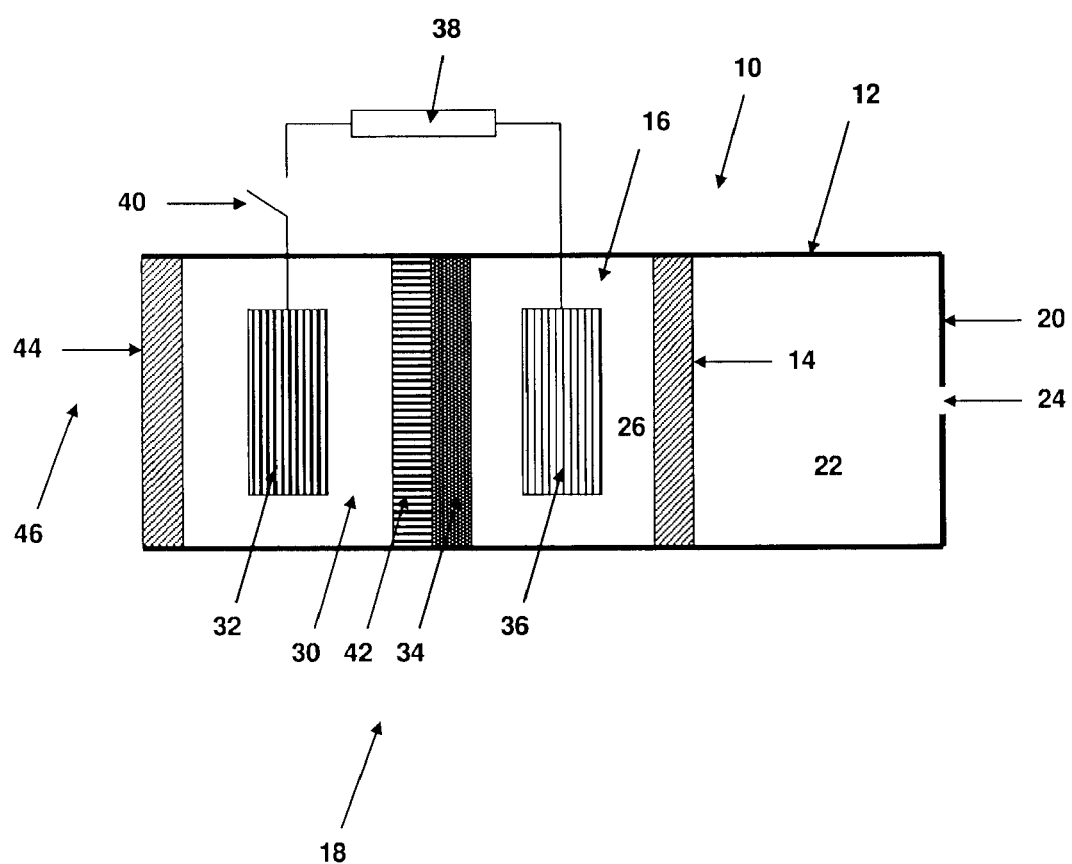
FIG. 11 depicts a cross-sectional side view of an alternate embodiment of a fluid delivery device having a self-contained auxiliary electrode compartment with a retractable piston.

Referring to FIG. 11, the water or saline may be self-contained in the auxiliary electrode compartment 30 without any migration of water from the external source 46.

In this case, either a displaceable member 44 retracts or the flexible auxiliary electrode compartment 30 collapses around the auxiliary electrode 32 on transfer of water from the auxiliary electrode compartment 30 to the active electrode chamber 16 via electro-osmosis. In addition, the auxiliary electrode 32 can be exposed directly to fluid.

In an embodiment incorporating an anionic exchange membrane 34, the auxiliary electrode 32 can be a porous cathode pellet that can be readily reduced when coupled with the active metal anode 36. The auxiliary electrode 32 may be fabricated from porous silver chloride, manganese dioxide, or other materials that can be readily reduced or may catalyze reduction reaction (e.g., reduction of oxygen or evolution of gaseous hydrogen from water) when coupled with the active metal anode 36. The active metal anode 36 can be a solid pellet, mesh, or metal powder type electrode fabricated from zinc, iron, magnesium, aluminum, silver, or another corrosion stable metal or alloy. Although not shown, the auxiliary electrode 32 may include a conventional current collector, such as a screen, a mesh, or a wire current collector fabricated from silver, titanium, platinum, or another corrosion stable metal. If the auxiliary electrode reaction is hydrogen evolution or oxygen reduction, then the auxiliary electrode 32 may be made from active carbon with or without catalysts such as Pt or Ni. The active metal anode 36 may also include a conventional current collector, such as a screen, a mesh or a wire current collector fabricated from the same metal as that of the active metal anode, or it may be fabricated from other metals such as brass, which is coated with the same metal as is the active anode metal. While specific examples of electrode materials and current collectors are described herein, it is to be understood that other electrode materials known to those with ordinary skill in the art having the present disclosure before them are likewise contemplated for use.

The anion exchange membrane 34 is positioned between the first electrode 32 and the active electrode 36. The anion exchange materials from which the membrane 34 may be made are well known in the art and do not require extensive elaboration. In brief, these materials are cross-linked polymer resins of the strong base type. In some embodiments, the resins are copolymers of styrene and di-vinyl benzene having quaternary ammonium ion as the charge group, which have a high selectivity for chloride ions and high resistance to organic fouling. Such anionic membranes are, for example, Neosepta-type membranes, which are commercially available from AMERIDIA (www.ameridia.com).

In an embodiment incorporating a cationic exchange membrane, the auxiliary electrode 32, the cationic exchange membrane 34, and the active electrode 36 are respectively positioned adjacent to the protective porous separator 28. The auxiliary electrode 32 need not be positioned inside the device 10 and can be positioned either on the outside wall of the device or entirely away from the housing 20, as shown in FIGS. 9 and 10. Alternatively, the water or saline may be self-contained in the auxiliary electrode compartment 30 without any migration of water from the external source 46. The auxiliary electrode 32 can be a solid pellet, mesh, or metal powder type electrode that is fabricated from zinc, iron, magnesium, aluminum, or another corrosion stable metal or alloy. The active metal anode 36 is a porous cathode pellet that can be readily reduced when coupled with the active metal anode 36. The auxiliary electrode 32 may be fabricated from porous silver chloride, manganese dioxide, or other materials that can be readily reduced, or may catalyze reduction reaction (e.g., reduction of oxygen or evolution of gaseous hydrogen from water) when coupled with the active metal anode. Although not shown, the auxiliary metal anode 32 may also include a conventional current collector such as a screen, a mesh, or a wire current collectors fabricated from the same metal as that of the active metal anode 36, or it may be fabricated from other metals such as brass, which is coated with the same metal as is the active anode metal. The active electrode 36 may also include a conventional current collector such as a screen, a mesh, or a wire current collectors fabricated from silver, titanium, platinum, or another corrosion stable metal. While specific examples of electrode materials and current collectors are described herein for illustrative purposes, it is to be understood that other electrode materials known to those with ordinary skill in the art having the present disclosure before them are likewise contemplated for use.

Referring again to FIG. 1, the ion-exchange membrane 34 (e.g., cation exchange membrane), is positioned between the auxiliary electrode 32 and the active electrode 36. The cation exchange materials from which the membrane 34 may be constructed are well known in the art and do not require extensive elaboration. In some embodiments, these materials are cross-linked polymer resins of the strong base type. In some embodiments, the resins include copolymers of styrene and di-vinyl benzene having sulfonate ion as the charge group, which have a high selectivity for sodium ions. Such commercial cationic membranes (e.g., Nafion type membranes) are available from Dupont®.

In operation, embodiments of the fluid delivery device 10 can deliver a fluid 22 in accordance with the following process. Initially, the activation switch 40 is actuated, whereupon an electrical circuit is complete and causes electrode reactions to take place at the electrodes 32, 36, and water to be extracted from the external environment 46; and, ultimately to be driven across ion-exchange membrane 34 into the electrical pump product chamber 16. Thus, water from the external environment 46 such as a human body diffuses through the protective porous separator 28 and into the auxiliary electrode compartment 30. Alternatively, the auxiliary electrode 32 need not be positioned inside the device and can be positioned either on the outside wall of the device or entirely away from the housing. In that case the ion-exchange membrane 34 is directly exposed to the body fluid, and a porous separator 28 can be placed directly adjacent to the ion-exchange membrane to prevent adverse effects from such exposure. In addition, the water or saline may be self-contained in the auxiliary electrode compartment 30 without any migration of water from the external source 46.

As one example, the reaction(s) associated with an embodiment of the fluid delivery device utilizing an anionic membrane 34 is now described in which the auxiliary electrode 32 is made of silver chloride and the active electrode 36 is made of zinc. At first, the electrode silver chloride is reduced to metallic silver, thus releasing chloride ions into solution according to the equation:

$$2AgCl + 2e^- \rightarrow 2Ag + 2Cl^- \qquad (1)$$

The chloride ions subsequently formed are dissolved in water and migrate under the influence of the electric field through the ion-exchange membrane 34 towards the active electrode 36 in the electrical pump product chamber 16. At the active electrode 36, zinc is dissolved according to the equation:

$$Zn \rightarrow Zn^{2+} + 2e^- \qquad (2)$$

The zinc ions thus formed react with incoming chloride ions forming zinc chloride according to the equation:

$$Zn^{2+} + 2Cl^- \rightarrow ZnCl_2 \qquad (3)$$

In addition to the electrochemical formation of zinc chloride according to the equation (3), during passage of the chloride ions through the membrane, water is entrained with the chloride ions so that an additional amount of water is produced at the opposite side of the membrane 34. This water transport is known in the art as electro-osmotic transport. Since the anionic membrane is selective for anions, only anions can pass through the membrane. Therefore, water may be transported through the membrane only in one direction.

The steady buildup of ion concentration in the electrochemical pump product chamber 16 due to the continuous formation of zinc chloride induces further water transport through osmotic effect. However, the ion-exchange membrane 34 allows back diffusion of the zinc chloride molecules from the electrochemical product chamber 16 to the auxiliary electrode compartment 30. The extent of back-diffusion depends on the properties of the ion-exchange membrane 34 and the concentration difference between the electrochemical product chamber 16 and the auxiliary electrode compartment 30. Thus, an equilibrium concentration of zinc chloride is established in the electrochemical pump product chamber 16 resulting in water transport via osmotic effect. A steady-state flux of water transport into the electrochemical pump product chamber 16 by combined electro-osmotic and osmotic effects is thus established. It should be noted that the osmotic flux is the result of the electro-osmotic flux, which establishes the concentration gradient. Therefore, the osmotic flux can be modified by virtue of modifying the electro-osmotic driving force. This is not possible with osmosis based devices and so their delivery rate is not adjustable. The water molecules transported into the electrochemical pump product chamber 16 generate pressure within the electrochemical pump product chamber 16. The pressure build-up causes some back transport of water from the electrochemical pump product chamber 16 to the auxiliary electrode compartment 30.

The steady-state flux obtained for a given ion-exchange membrane can be expressed in terms of the following mathematical equation:

$$J_{Steady\ State\ Flux} = J_{eof} + J_{of} - J_{bdf} - J_{hf} \qquad (I)$$

where, $J_{eof}$ = electro-osmotic flux
$J_{of}$ = osmotic flux
$J_{bdf}$ = back diffusion flux
$J_{hf}$ = hydraulic flux As another example, the reaction(s) associated with an embodiment of the fluid delivery device utilizing a cationic membrane 34 is now described in which the auxiliary electrode 32 is made of zinc and the active electrode 36 is made of silver chloride. At first, the electrode zinc is dissolved according to the equation:

$$Zn \rightarrow Zn^{2+} + 2e^- \qquad (4)$$

Sodium ions present in the saline solution migrate under the influence of the electric field through the ion exchange membrane 34 towards the active electrode 36 in the electrical pump product chamber 16. At the active electrode 36, silver chloride is reduced to metallic silver releasing chloride ions into solution according to the equation:

$$2AgCl + 2e^- \rightarrow 2Ag + 2Cl^- \qquad (5)$$

The migrated sodium ions react with the chloride ions forming sodium chloride according to the equation:

$$Na^+ + Cl^- \rightarrow NaCl \qquad (6)$$

In addition to the electrochemical formation of sodium chloride according to the equation (6), during passage of the sodium ions through the membrane, water is electro-osmotically transported with sodium ions so that an additional amount of water is produced at the opposite side of the membrane 34. Since the cationic membrane 34 is selective for cations, only cations can pass through the membrane. Therefore, water may be transported through the membrane only in one direction.

Due to the continuous formation of sodium chloride, the steady buildup of ion concentration in the electrochemical pump product chamber 16 induces further water transport through osmotic effect. However, the ion-exchange membrane 34 allows back diffusion of sodium chloride molecules from the electrochemical product chamber 16 to the auxiliary electrode compartment 30. The extent of back-diffusion depends on the properties of the ion-exchange membrane 34 and the concentration difference between the electrochemical product chamber 16 and the auxiliary electrode compartment 30. Thus, an equilibrium concentration of sodium chloride is established in the electrochemical pump product chamber 16 resulting in water transport by the osmotic effect. A steady-state flux of water transport into the electrochemical pump product chamber 16 is established by the combined electro-osmotic and osmotic effects. It should be noted that the osmotic flux is the result of the electro-osmotic flux, which establishes the concentration gradient. Therefore, the osmotic flux can be modified by virtue of modifying the electro-osmotic driving force. This is not possible with osmosis-only based devices and so their delivery rate is not adjustable. The water molecules transported into the electrochemical pump product chamber 16 generate pressure within the electrochemical pump product chamber 16. The pressure build-up causes some back transport of water from the electrochemical pump product chamber 16 to the auxiliary electrode compartment 30. The steady state flux obtained for a given ion-exchange membrane 34 can be expressed in terms of the same mathematical equation I shown above.

Both embodiments described above are capable of generating high pressure within the electrochemical pump product chamber 16. High pressure is desired to deliver viscous formulations and to also produce delivery that is less sensitive to the ambient pressure changes. The high pressure in the device 10 can be created either by outlet orifice restriction using a pressure relief valve, a duck bill valve, a ball and spring, a restricted catheter, a tortuous path, a flow moderator, or diffuse membrane (refer to FIG. 12), or from the displaceable member 14 using a stiff bag, bellows, diaphragm, or from piston friction with the inner walls of the device.

Figure 12:
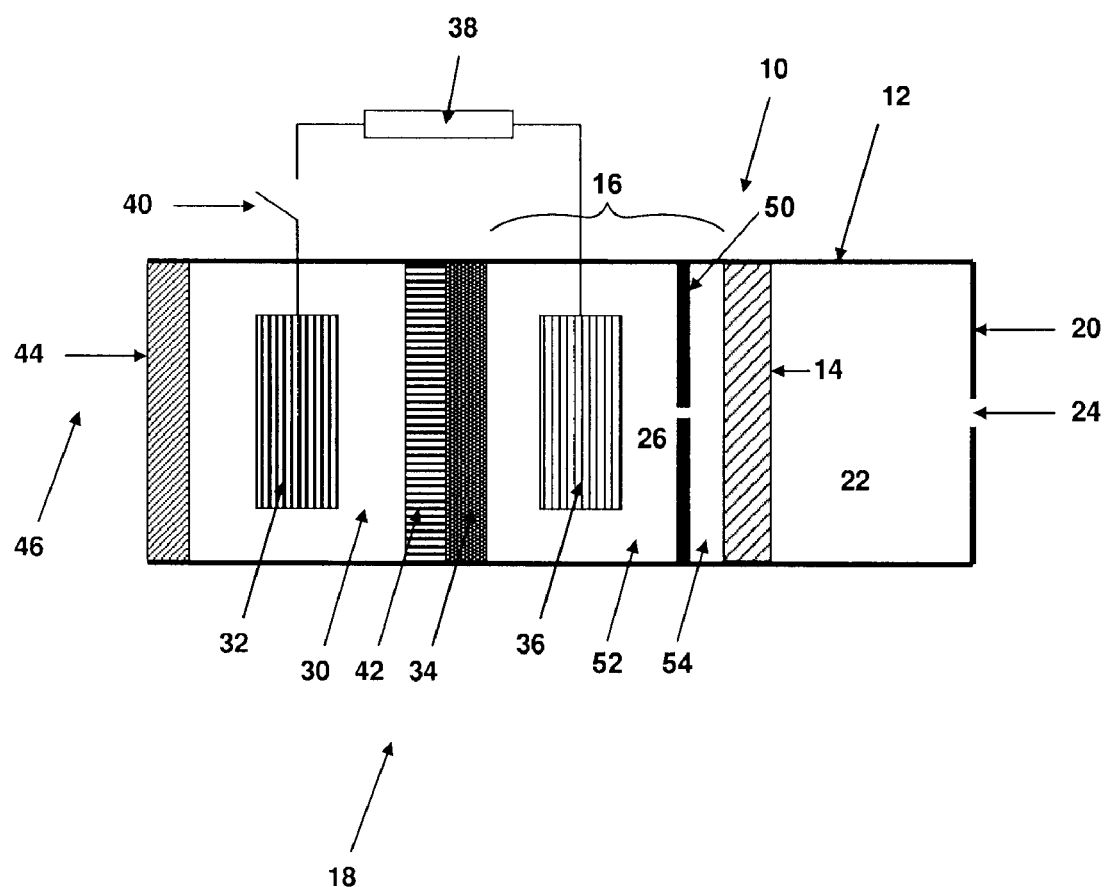
FIG. 12 depicts a cross-sectional view of an alternative embodiment of a fluid delivery device having a diffusion membrane to provide an improved response time.

FIG. 12 depicts a cross-sectional view of an alternative embodiment of a fluid delivery device 10 having a diffusion membrane 50 to provide an improved response time. In the illustrated embodiment, the diffusion membrane 50 is located within the electrochemical pump product chamber 16, between the ion-exchange membrane 34 and the displaceable member 14. In this way, the diffusion membrane 50 subdivides the electrochemical pump product chamber 16 into a first chamber portion 52 and a second chamber portion 54. In other embodiments, more than one diffuse membrane 50 may be implemented to subdivide the electrochemical pump product chamber 16 into more than two chamber portions. In some embodiments, at least one of the diffuse membranes 50 may be located between the ion-exchange membrane 34 and the active electrode 36.

In general, the diffuse membrane 50 acts as a barrier between the first and second chamber portions 52 and 54. However, the diffuse membrane 50 has one or more holes, or channels, through the thickness of the diffuse membrane 50 so that fluid can pass through the diffuse membrane 50 by way of advection in the presence of electro-osmosis through the ion-exchange membrane 34. In contrast, the diffuse membrane 50 prevents substantially all advection of fluid in the absence of electro-osmosis through the ion-exchange membrane.

Additionally, because of the presence of the diffuse membrane 50 within the electrochemical pump product chamber 16, osmosis quickly dilutes the solution in the first chamber portion 52 in order to achieve a response time more quickly than if the diffuse membrane 50 were not present. For reference, the response time refers to the time duration between the moment the controller 38 turns off the electrochemical pump (to stop electro-osmostic transport) and the time the flux reaches a predetermined level. For example, a 90% response time is the time duration that it takes for the flux to reach 10% (i.e., 1-90%=10%). Thus, the placement of the diffuse membrane 50 within the electrochemical pump product chamber 16 allows the osmotic process to achieve a response time faster because the osmotic process can be performed on predominantly on the fluid in the first chamber portion 52, rather than all of the fluid within the entire electrochemical pump product chamber 16.

As an additional benefit of some embodiments, the startup response time of the fluid delivery device 10 also may be reduced due to the introduction of the diffuse membrane 50. This is because the osmosis component of the flux response to the concentration in the first chamber portion 52, rather than the concentration in the overall electrochemical pump product chamber 16. The smaller volume reaches steady state much quicker than the overall volume. Hence, embodiments described herein provide an improved response time when the electro-osmotic rate is adjusted by reducing the effects of the residual osmotic transport process.

Figure 13A:
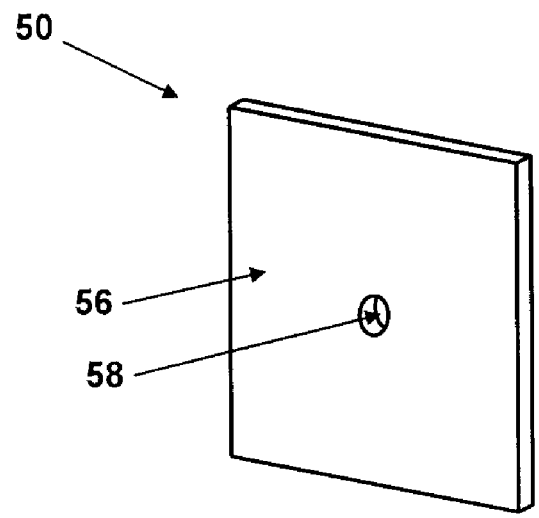
FIGS. 13A and 13B depict perspective views of embodiments of the diffusion membrane of FIG. 12.
Figure 13B:
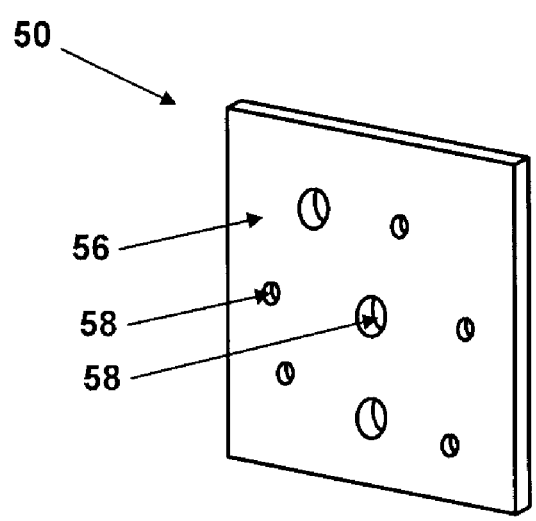

FIGS. 13A and 13B depict perspective views of embodiments of the diffusion membrane 50 of FIG. 12. In both of the illustrated embodiments, the diffuse membrane 50 includes a substantially planar plate 56 with one or more holes 58 defined therein. Where multiple holes 58 are implemented, the holes 58 may be of the same or different sizes. Additionally, in some embodiments, the holes 58 may pass directly (i.e., linearly) through the plate 56. In other embodiments, the holes 58 may follow tortuous (i.e., non-linear) paths from one side of the plate 56 to the other.

The overall geometric shape of the plate 56 substantially matches the cross-sectional opening of the electrochemical pump product chamber 16. Although the illustrated diffuse membranes 50 use rectangular plates 56, other embodiments may have other physical shapes and/or dimensions. Additionally, some embodiments may implement the diffuse membrane 50 having a geometry that is non-planar.

Figure 6:
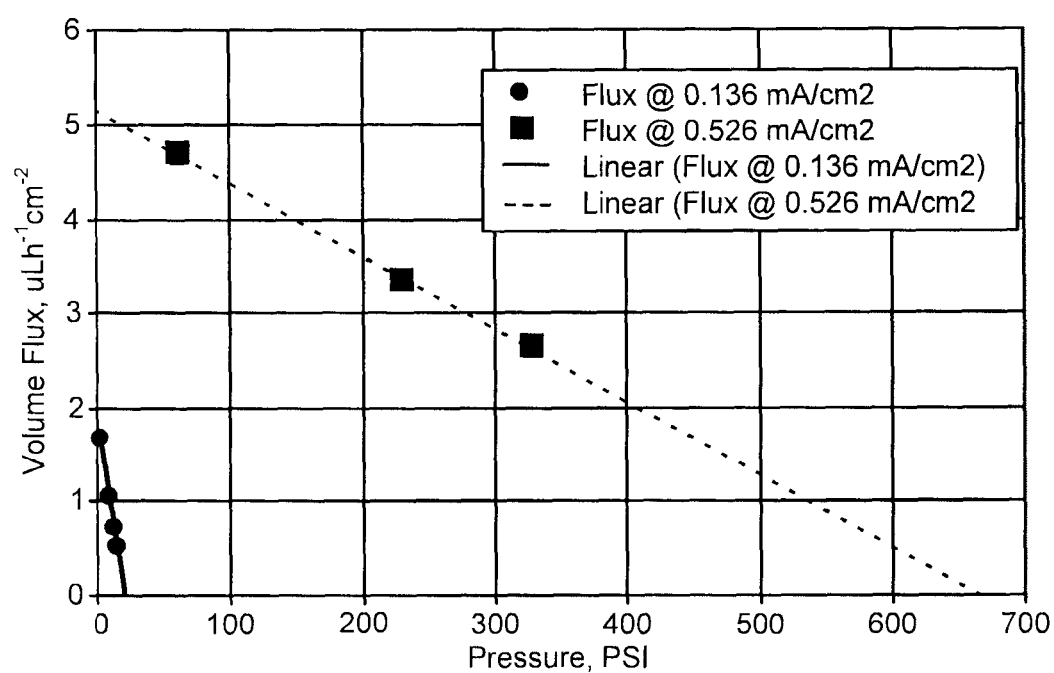
FIG. 6 depicts a graph of volume flux vs. pressure applied to the electrochemical product chamber at two different current density values for one embodiment of a fluid delivery device having an anionic exchange membrane fabricated in accordance with the following cell parameters: Neosepta® AFN ion exchange membrane, solid zinc anode, silver chloride cathode, 0.9% NaCl electrolyte.
Figure 7:
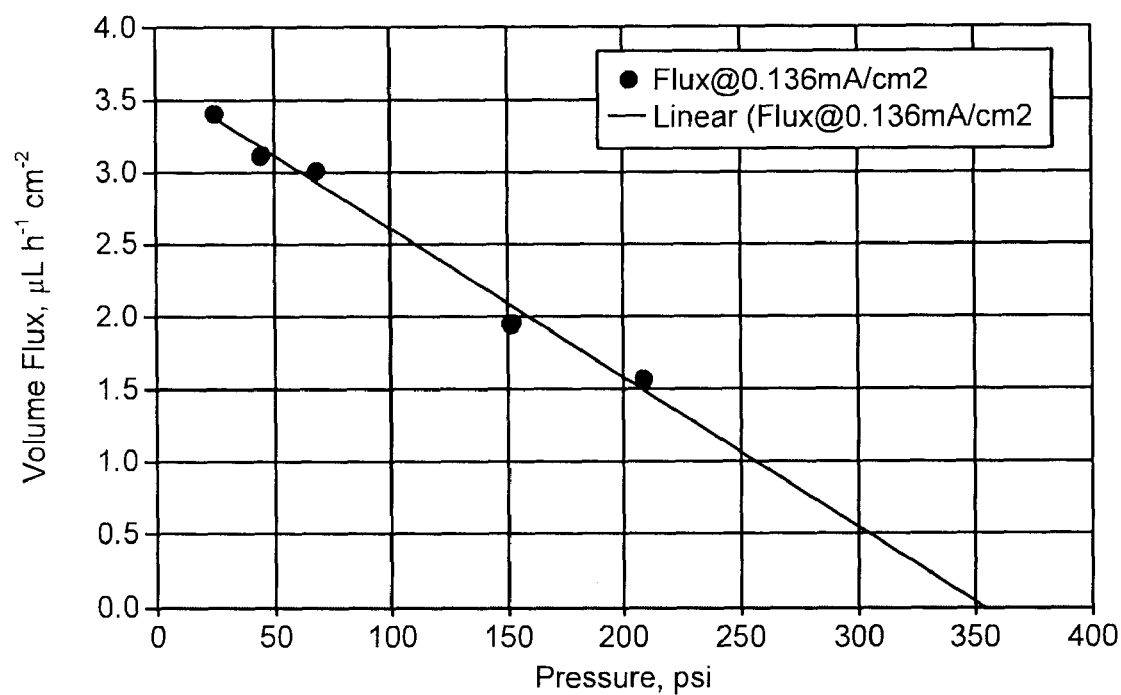
FIG. 7 depicts a graph of volume flux vs. pressure applied to the electrochemical product chamber at two different current density values for one embodiment of a fluid delivery device having an cationic exchange membrane fabricated in accordance with the following cell parameters: NAFION® 117 cation exchange membrane, solid zinc anode, silver chloride cathode, 0.9% NaCl electrolyte.
Figure 8:
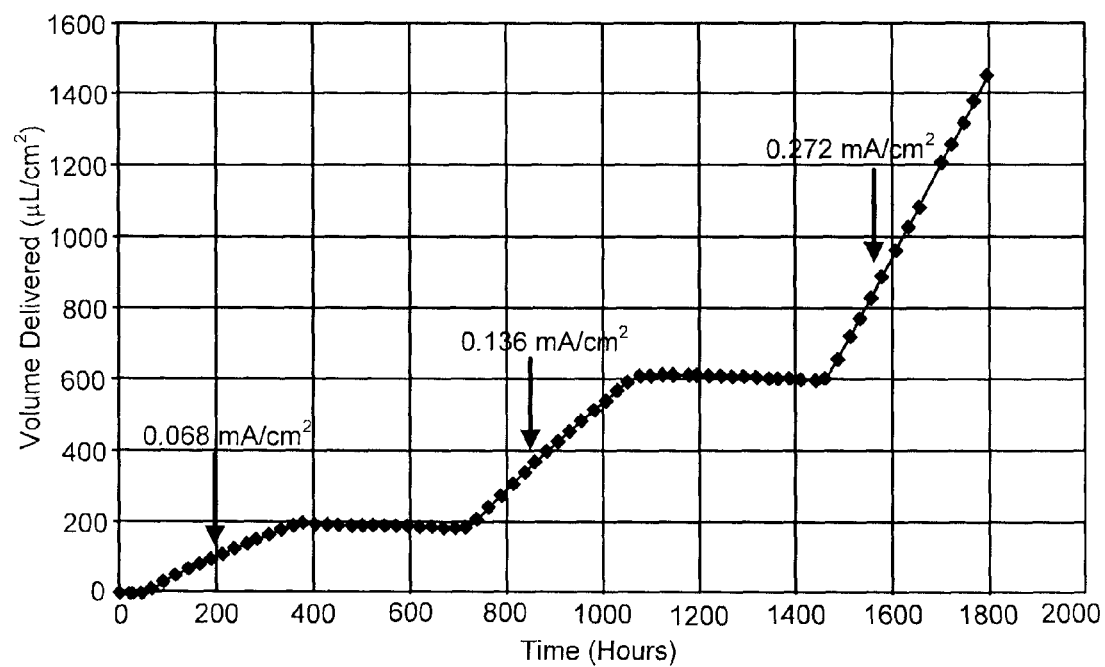
FIG. 8 depicts a graph of volume delivered vs. test time for one embodiment of a fluid delivery device fabricated in accordance with the following cell parameters: Neosepta® AFN ion exchange membrane, solid zinc anode, silver chloride cathode, 0.9% NaCl electrolyte, in which data is recorded at three different current density values with no current steps in-between in which the different slopes at different current densities show that the flow-rate can be adjusted.

The pressure generated by the first embodiment of the fluid delivery device 10 discussed above is shown in FIG. 6, in which the maximum pressure ($P_{max}$, the pressure at which the flux becomes zero) that can be achieved is 20 psi at 0.136 mA/cm$^2$. Operation at 3.8 times the current density (0.525 mA/cm$^2$) provides a $P_{max}$ of 700 psi. In the case of the second embodiment of the fluid delivery device 10, FIG. 7 shows $P_{max}$ to be 350 psi at 0.136 mA/cm$^2$.

The generated pressure, in turn, imparts a force upon the displaceable member 14. The displaceable member 14 is displaced laterally away from the electrochemical pump product chamber 16, which controllably expels fluid from the reservoir 12.

It is to be understood that the above-identified device and process embodiments enable a controlled delivery of a fluid over an extended period of time at a relatively precise and accurate rate inasmuch as the water transported is proportional to the current, which in turn depends on the value of the resistor, or on the signal output from the electrical controller 38. Therefore, the fluid delivery rate of the fluid deliver device 10 is controlled by selection of the resistor or on the signal output from the electrical controller 38 and not by the rate at which water is permitted to enter the housing via convection action of the protective porous separator 28. It is also to be understood that the fluid delivery rate, or a fluid delivery rate profile (e.g., pulsing) can be facilely varied by other means including, but not limited to, selecting resistors with different resistance values or by changing the signal output from the electrical controller 38.

Figure 2:
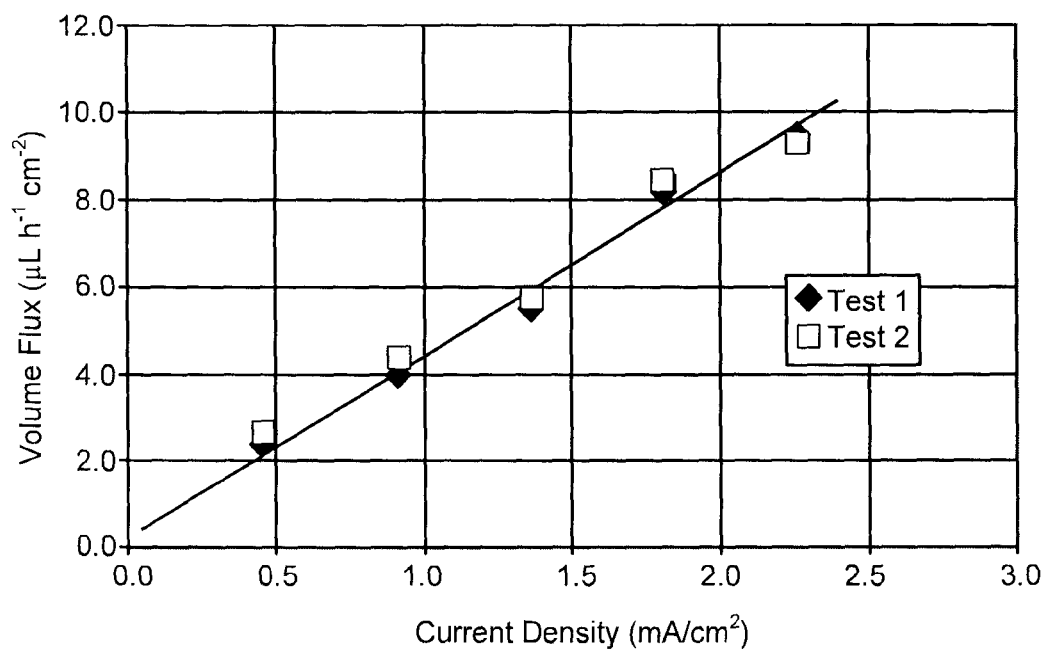
FIG. 2 depicts a graph of volume flux versus current density in the volume flux range from 2.0 to 10.0 $\mu L\ h^{-1}\ cm^{-2}$ for one embodiment of a fluid delivery device having an anionic exchange membrane fabricated in accordance with the following cell parameters: AMI 7001 ion exchange membrane, powder zinc anode, nickel mesh cathode, 0.9% NaCl electrolyte.
Figure 3:
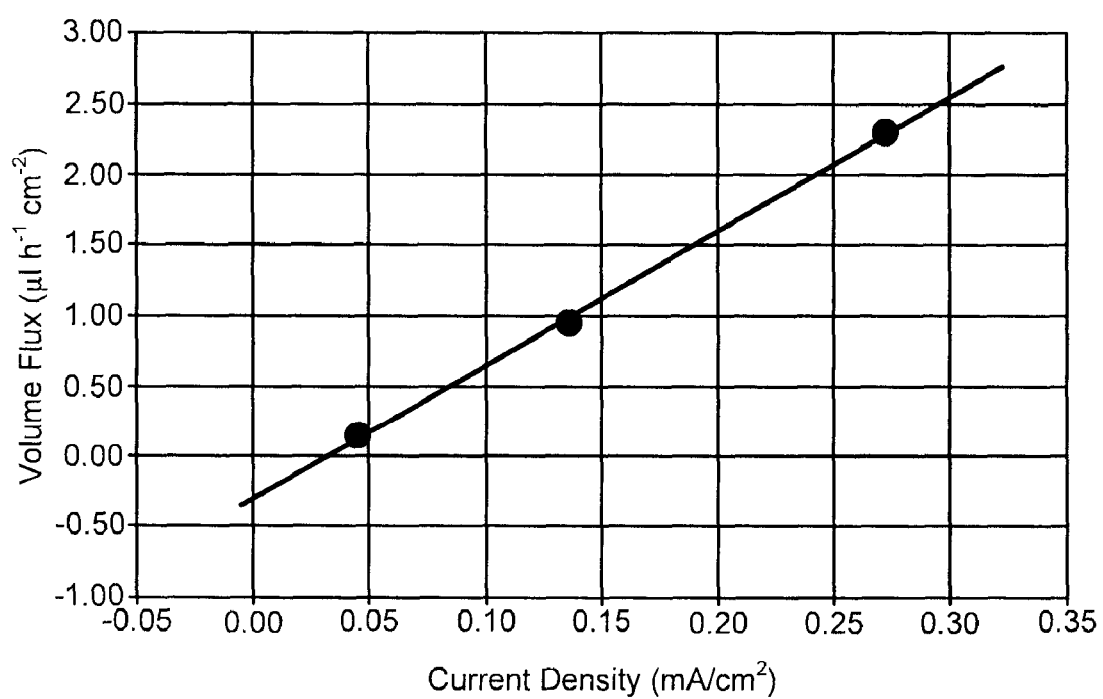
FIG. 3 depicts a graph of volume flux versus current density in the volume flux range from 0 to 2.5 $\mu L\ h^{-1} cm^{-2}$ for one embodiment of a fluid delivery device having an anionic exchange membrane fabricated in accordance with the following cell parameters: Neosepta® AFN ion exchange membrane, solid zinc anode, silver chloride cathode, 0.9% NaCl electrolyte.
Figure 4:
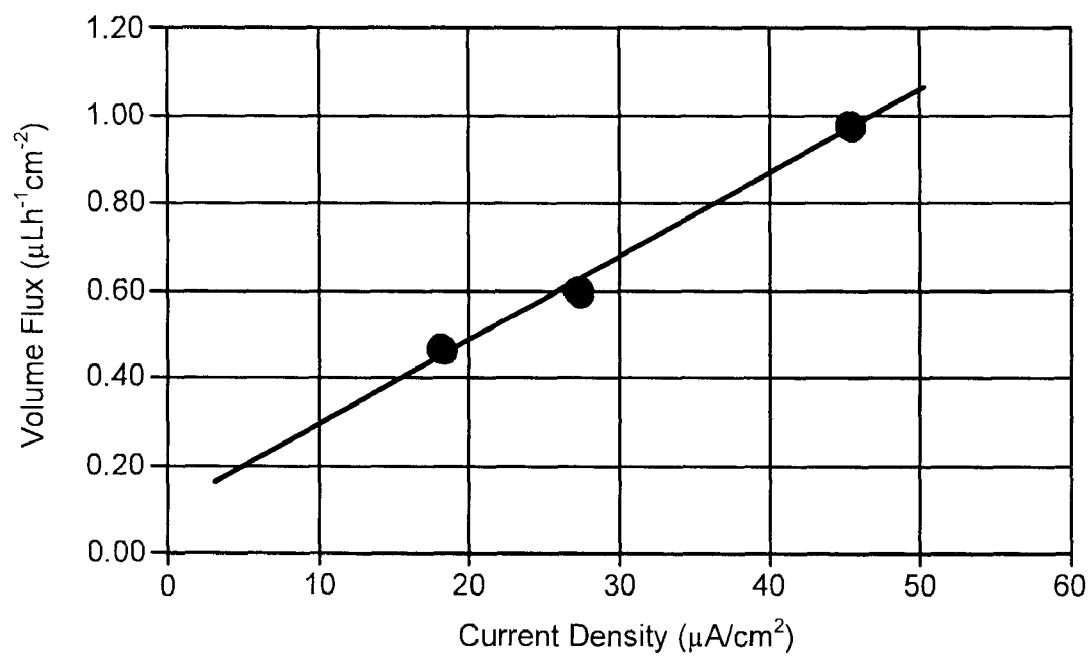
FIG. 4 depicts a graph of volume flux versus current density in the volume flux range from 0.5 to 2.5 $\mu L\ h^{-1}\ cm^{-2}$ for one embodiment of a fluid delivery device having an anionic exchange membrane fabricated in accordance with the following cell parameters: Neosepta® AMX ion exchange membrane, solid zinc anode, silver chloride cathode, 0.9% NaCl electrolyte.
Figure 5:
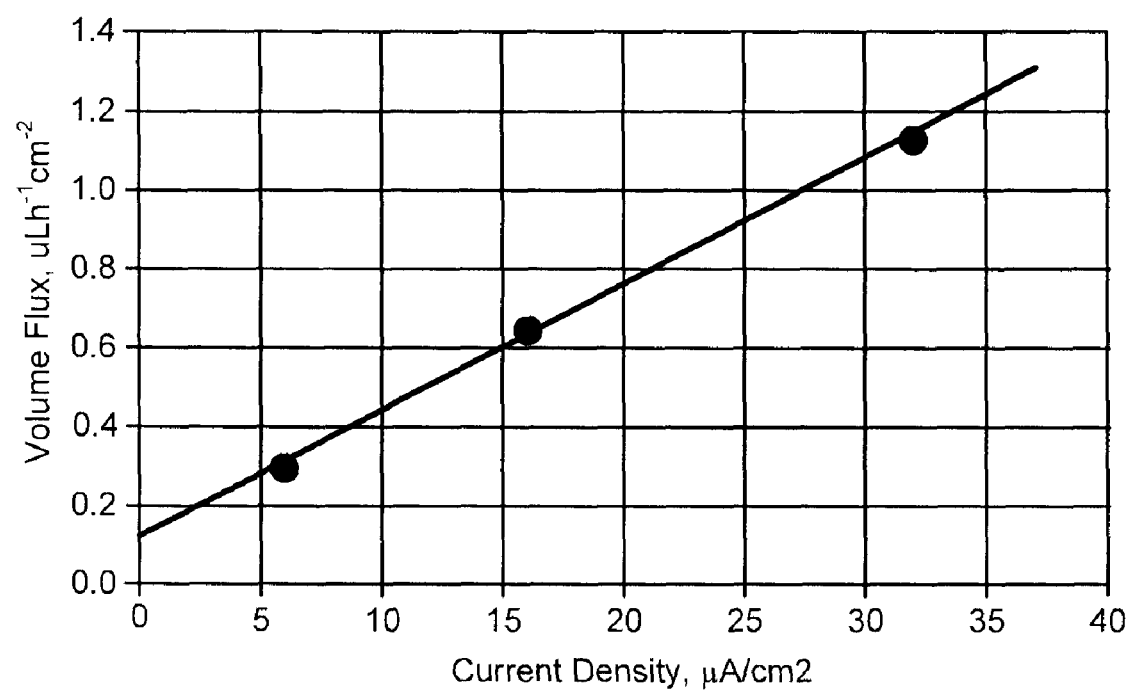
FIG. 5 depicts a graph of volume flux versus current density in the volume flux range from 0.2 to 1.2 $\mu L\ h^{-1}\ cm^{-2}$ for one embodiment of a fluid delivery device having an cationic exchange membrane fabricated in accordance with the following cell parameters: NAFION® 117 cation exchange membrane, solid zinc anode, silver chloride cathode, 0.9% NaCl electrolyte.

For the embodiments illustrated in the drawings, a linear relationship between volume flux and current density may be obtained at high and low volume fluxes. This is illustrated in the case of first embodiment in FIG. 2 for volume flux ranging from 2.0 to 10.0 μL h$^{-1}$ cm$^{-2}$; and in FIG. 3 for volume flux ranging from 0.1 to 2.5 μL h$^{-1}$ cm$^{-2}$. The current density required to produce such volume fluxes depends on the membrane type used and, in some embodiments, may be as low as 20 μA cm$^{-2}$ to produce a volume flux of 0.5 μL h$^{-1}$ cm$^{-2}$, as shown in FIG. 4. Another feature of some embodiments, including the embodiment shown in FIG. 1, is high stability operation over more than 1000 hours of operation.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A fluid delivery device, comprising:
   an electrochemical pump for transporting water, the electrochemical pump comprising an electrochemical pump product chamber configured to retain water transported by the electrochemical pump, an active electrode, an auxiliary electrode configured for ionic communication with the active electrode, an ion-exchange membrane positioned between the active electrode and the auxiliary electrode, wherein the ion-exchange membrane is configured to transport water by osmosis and electro-osmosis between the active electrode and the auxiliary electrode into the electrochemical pump product chamber, wherein one of the electrodes is located in the first chamber portion of the electrochemical pump product chamber, and the other electrode is located on an opposite side of the ion-exchange membrane;
a reservoir configured to contain a fluid to be delivered;
a displaceable member positioned between the electrochemical pump product chamber and the reservoir, wherein the displaceable member is responsive to the electrochemical pump transporting water into the electrochemical pump product chamber; and
a diffuse membrane configured to generate increased pressure within the electrochemical pump product chamber, wherein the diffuse membrane is located within the electrochemical pump product chamber, wherein the diffuse membrane at least partially defines a first chamber portion and a second chamber portion within the electrochemical pump product chamber, and wherein the diffuse membrane comprises a substantially planar barrier with at least one hole therethrough having cross-sectional dimensions to prevent substantially all advection of water from the first chamber portion to the second chamber portion in the absence of electro-osmosis through the ion-exchange membrane.

2. The fluid delivery device of claim 1, wherein the electrochemical pump further comprises a controller coupled to the active electrode and the auxiliary electrode, wherein the controller is configured to generate an electrical current and facilitate water transport through the ion-exchange membrane in response to the electrical current.

3. The fluid delivery device of claim 2, wherein the construction of the fluid delivery device is suitable for implantation within a living body.

4. The fluid delivery device of claim 3, wherein the controller is configured to be capable of remote adjustment external to the living body.

5. The fluid delivery device of claim 2, wherein the controller is configured to be capable of varying a fluid delivery rate in response to varying a resistance of the controller.

6. The fluid delivery device of claim 1, further comprising a housing to contain the active electrode and the auxiliary electrode of the electrochemical pump, the electrochemical pump product chamber of the electrochemical pump, the diffuse membrane of the electrochemical pump, the displaceable member, and the reservoir.

7. The fluid delivery device according to claim 6, wherein, the auxiliary electrode is positioned within the housing.

8. The fluid delivery device of claim 6, further comprising a separator being permeable to $H_2O$ molecules or saline, the separator being attached to the housing, wherein the separator is configured for direct contact with a body tissue or fluid when the fluid delivery device is inserted within a living body, and one or more of either electrode or the ion-exchange membrane is indirectly exposed and not in direct contact with the body tissue or fluid.

9. The fluid delivery device of claim 6, wherein the housing defines a plurality of apertures, wherein at least one aperture is located at the reservoir to allow the fluid to exit the reservoir.

10. The fluid delivery device of claim 9, further comprising at least one catheter operably connected to the aperture at the reservoir.

11. The fluid delivery device of claim 10, wherein the at least one catheter is flexible.

12. The fluid delivery device of claim 10, wherein the at least one catheter is perforated.

13. The fluid delivery device of claim 10, wherein the at least one catheter comprises a diffusive outlet.

14. The fluid delivery device of claim 10, wherein the at least one catheter comprises a check valve.

15. The fluid delivery device according to claim 6, further comprising a housing to contain the active electrode, the electrochemical pump product chamber of the electrochemical pump, the diffuse membrane of the electrochemical pump, the displaceable member, and the reservoir, wherein, the auxiliary electrode of the electrochemical pump is positioned external to the housing.

16. The fluid delivery device of claim 1, further comprising:
a galvanic couple comprising the auxiliary electrode and active electrode.

17. The fluid delivery device of claim 1, wherein the ion exchange membrane is an anionic or cationic type.

18. The fluid delivery device of claim 1, wherein the ion-exchange membrane is a polymer or ceramic material.

19. The fluid delivery device of claim 1, wherein the ion-exchange membrane includes a geometry being a sheet, a hollow fiber, or a tube.

20. The fluid delivery device of claim 1, further including a second or multiple ion-exchange membrane.

21. The fluid delivery device of claim 20, wherein the ion-exchange membranes are of similar type.

22. The fluid delivery device of claim 20, wherein the ion-exchange membranes are of different type.

23. The fluid delivery device of claim 1, further comprising:
an auxiliary electrode compartment being impermeable to body fluid, the auxiliary electrode compartment containing saline and the auxiliary electrode; and
a second displaceable member to define at least a portion of the auxiliary electrode compartment, wherein the second displaceable member is configured to retract in response to transfer of water from the auxiliary electrode compartment through the ion-conducting membrane to the electrochemical pump product chamber.

24. The fluid delivery device of claim 1, further comprising:
an auxiliary electrode compartment being impermeable to body fluid, the auxiliary electrode compartment containing saline and the auxiliary electrode, wherein the auxiliary electrode compartment is configured to collapse in response to transfer of water from the auxiliary electrode compartment through the ion-conducting membrane to the electrochemical pump product chamber.

25. The fluid delivery device according to claim 1, wherein the electrochemical pump further comprises an activation switch for operating the fluid delivery device.

26. The fluid delivery device of claim 25, wherein the activation switch is of an ionic, electronic, or mechanical type.

27. The fluid delivery device of claim 25, wherein the activation switch is controlled by the controller.

28. The fluid delivery device of claim 1, wherein the electrochemical pump further comprises a support member for supporting the ion-exchange membrane.

29. The fluid delivery device of claim 28, wherein the support member is a porous solid material selected from the group consisting of plastic, ceramic, glass, corrosion stable metal, and a combination thereof.

30. The fluid delivery device of claim 28, wherein the support member comprises a structure selected from the group consisting of fabric, perforated plate, and mesh.

31. The fluid delivery device of claim 28, wherein the support member has a geometry being flat, concave, convex, or tubular.

32. The fluid delivery device of claim 1, wherein the displaceable member is selected from the group consisting of a piston, a bladder, a flexible bag, a bellows, a diaphragm, a plunger, and a combination thereof.

33. The fluid delivery device of claim 32, wherein the piston comprises a tubing and a plunger.

34. The fluid delivery device of claim 33, wherein the plunger comprises a ball, a bubble, a solid, a separating fluid, a bung, or a gel.

35. The fluid delivery device of claim 1, wherein the fluid to be delivered comprises a biological, a drug, a lubricant, a fragrant fluid, a chemical agent, or a mixture thereof.

36. The fluid delivery device of claim 1 wherein the fluid is homogenous.

37. The fluid delivery device of claim 1 wherein the fluid is layered to provide intermittent delivery of an active or multiple and different actives.

38. The fluid delivery device of claim 1, wherein the fluid comprises a gel, a paste, or a suspension with or without dispersant.

39. A fluid delivery device suitable for implantation within a living body, the fluid delivery device comprising:
   an electrochemical pump for transporting water, the electrochemical pump comprising an electrochemical pump product chamber configured to retain water transported by the electrochemical pump;
   a control circuit operably connected to the electrochemical pump, wherein a rate of water transport being responsive to electrical current flowing through the control circuit;
   an active electrode and an auxiliary electrode being in ionic communication with each other and operably connected to the control circuit;
   a reservoir configured to contain a fluid to be delivered;
   a displaceable member positioned between the electrochemical pump product chamber and the reservoir, wherein the displaceable member is responsive to the electrochemical pump transporting water into the electrochemical pump product chamber;
   an ion-exchange membrane positioned between the active electrode and the auxiliary electrode, wherein the ion-exchange membrane is configured to transport water by osmosis and electro-osmosis between the active electrode and the auxiliary electrode into the electrochemical pump product chamber;
   a diffuse membrane configured to generate increased pressure within the electrochemical pump product chamber, wherein the diffuse membrane comprises a substantially planar barrier with at least one hole therethrough having cross-sectional dimensions;
   a protective porous separator being permeable to $H_2O$ molecules or saline and positioned such that the active electrode or the ion-exchange membrane is indirectly exposed to body tissue or body fluids; and,
   a housing containing the electrochemical pump, the displaceable member, the diffuse membrane, and the reservoir therein, wherein the auxiliary electrode is external to the housing.

40. The fluid delivery device of claim 39, wherein the protective porous separator comprises a gel.

41. A method for delivering a fluid by a fluid delivery device suitable for implantation in a living body, the method comprising:
   transporting water through an ion-exchange membrane by osmosis and electro-osmosis using an electrochemical pump at a rate proportional to an output signal of a control circuit;
   expanding a volume of an electrochemical pump product chamber in response to transporting the water into the electrochemical pump product chamber;
   generating increased pressure within the expanded electrochemical pump product chamber using a diffuse membrane, wherein the diffuse membrane comprises a substantially planar barrier with at least one hole therethrough having cross-sectional dimensions;
   displacing a displaceable member in response to the pressure in the electrochemical pump product chamber; and
   controllably expelling fluid from the reservoir in response to displacement of the displaceable member.

42. The method of claim 41, further comprising adjusting a fluid delivery rate profile.

43. The method of claim 41, further comprising adjusting a fluid delivery rate.

44. The method of claim 43, wherein adjusting the fluid delivery rate further comprising changing the output signal of the control circuit.

45. The method of claim 41, further comprising activating a switch to control delivery of the fluid, wherein the switch is operably coupled between the active electrode and the auxiliary electrode.

46. A fluid delivery device, comprising:
   an electrochemical pump for transporting water, the electrochemical pump comprising:
      an electrochemical pump product chamber configured to retain water transported by the electrochemical pump;
      an active electrode;
      an auxiliary electrode configured for ionic communication with the active electrode; and
      an ion-exchange membrane positioned between the active electrode and the auxiliary electrode, wherein the ion-exchange membrane is configured to transport water by osmosis and electro-osmosis between the active electrode and the auxiliary electrode into the electrochemical pump product chamber, and wherein one of the electrodes is located in the first chamber portion of the electrochemical pump product chamber, and the other electrode is located on an opposite side of the ion-exchange membrane;
   a reservoir configured to contain a fluid to be delivered;
   a displaceable member positioned between the electrochemical pump product chamber and the reservoir, wherein the displaceable member is responsive to the electrochemical pump transporting water into the electrochemical pump product chamber;
   a diffuse membrane configured to generate increased pressure within the electrochemical pump product chamber, wherein the diffuse membrane is located within the electrochemical pump product chamber, and wherein the diffuse membrane at least partially defines a first chamber portion and a second chamber portion within the electrochemical pump product chamber;
   an auxiliary electrode compartment being impermeable to body fluid, the auxiliary electrode compartment containing saline and the auxiliary electrode; and
   a second displaceable member to define at least a portion of the auxiliary electrode compartment, wherein the second displaceable member is configured to retract in response to transfer of water from the auxiliary electrode compartment through the ion-conducting membrane to the electrochemical pump product chamber.

47. A fluid delivery device, comprising:
an electrochemical pump for transporting water, the electrochemical pump comprising:
   an electrochemical pump product chamber configured to retain water transported by the electrochemical pump;
   an active electrode;
   an auxiliary electrode configured for ionic communication with the active electrode; and
   an ion-exchange membrane positioned between the active electrode and the auxiliary electrode, wherein the ion-exchange membrane is configured to transport water by osmosis and electro-osmosis between the active electrode and the auxiliary electrode into the electrochemical pump product chamber, and wherein one of the electrodes is located in the first chamber portion of the electrochemical pump product chamber, and the other electrode is located on an opposite side of the ion-exchange membrane;
a reservoir configured to contain a fluid to be delivered;
a displaceable member positioned between the electrochemical pump product chamber and the reservoir, wherein the displaceable member is responsive to the electrochemical pump transporting water into the electrochemical pump product chamber; and
a diffuse membrane configured to generate increased pressure within the electrochemical pump product chamber, wherein the diffuse membrane is located within the electrochemical pump product chamber, and wherein the diffuse membrane at least partially defines a first chamber portion and a second chamber portion within the electrochemical pump product chamber; and
an auxiliary electrode compartment being impermeable to body fluid, the auxiliary electrode compartment containing saline and the auxiliary electrode, wherein the auxiliary electrode compartment is configured to collapse in response to transfer of water from the auxiliary electrode compartment through the ion-conducting membrane to the electrochemical pump product chamber.

* * * * *